(12) United States Patent
de Santis et al.

(10) Patent No.: US 10,213,337 B2
(45) Date of Patent: Feb. 26, 2019

(54) VITRECTOMY PROBE

(71) Applicant: Erre Quadro S.R.L., Pisa (IT)

(72) Inventors: Giovanni de Santis, Pisa (IT); Gualtiero Fantoni, Pisa (IT); Stanislao Rizzo, Lucca (IT); Francesco Faraldi, Turin (IT)

(73) Assignee: Erre Quadro S.R.L., Pisa (IT)

( * ) Notice: Subject to any disclaimer, the term of this patent is extended or adjusted under 35 U.S.C. 154(b) by 61 days.

(21) Appl. No.: 15/304,116

(22) PCT Filed: Apr. 14, 2015

(86) PCT No.: PCT/EP2015/025019
§ 371 (c)(1),
(2) Date: Oct. 14, 2016

(87) PCT Pub. No.: WO2015/158438
PCT Pub. Date: Oct. 22, 2015

(65) Prior Publication Data
US 2017/0027753 A1   Feb. 2, 2017

(30) Foreign Application Priority Data
Apr. 16, 2014 (IT) ................................ PI2014A0030

(51) Int. Cl.
*A61F 9/007* (2006.01)
(52) U.S. Cl.
CPC ...... *A61F 9/00745* (2013.01); *A61F 9/00763* (2013.01)
(58) Field of Classification Search
CPC .............. A61F 9/00745; A61F 9/00754; A61F 9/00763
See application file for complete search history.

(56) References Cited

U.S. PATENT DOCUMENTS

| 5,275,607 A | 1/1994 | Lo et al. |
| 5,630,827 A * | 5/1997 | Vijfvinkel .......... A61B 10/0266 604/22 |

(Continued)

FOREIGN PATENT DOCUMENTS

| WO | WO 1993005718 A1 | 4/1993 |
| WO | WO 2015158438 A1 | 10/2015 |

OTHER PUBLICATIONS

International Search Report and Written Opinion for PCT/EP2015/25019.

*Primary Examiner* — Tuan V Nguyen
(74) *Attorney, Agent, or Firm* — Woodard, Emhardt, Moriarty, McNett & Henry LLP

(57) ABSTRACT

Vitrectomy probe (1) for the removal of the vitreous humour (1a) and comprising a tube (2) adapted to be put into direct contact with the vitreous (1a), defining a main axis (2a) and including an internal passage (21) and a opening (23) enabling the vitreous (1a) to enter the internal passage (21) and comprising at least one cutting edge (23a, 23b); a suction system suitable for the creation of vacuum within the internal passage (21) sucking the vitreous (1a) into the opening (23); a drive unit adapted to move the tube (2) defining a vibrational motion (A) of the tube (2) which therefore produces pressure waves reducing the viscosity of the vitreous (1a), and a reciprocating motion (B), having a frequency lower than the frequency of the vibrational motion (A), adapted to enable the cutting edges (23a, 23b) to cut the vitreous (1a)

18 Claims, 4 Drawing Sheets

(56) References Cited

U.S. PATENT DOCUMENTS

| | | | |
|---|---|---|---|
| 6,007,513 A | 12/1999 | Anis et al. | |
| 6,283,974 B1 * | 9/2001 | Alexander | A61F 9/00745 604/22 |
| 2002/0099400 A1 * | 7/2002 | Wolf | A61F 9/00745 606/169 |

* cited by examiner

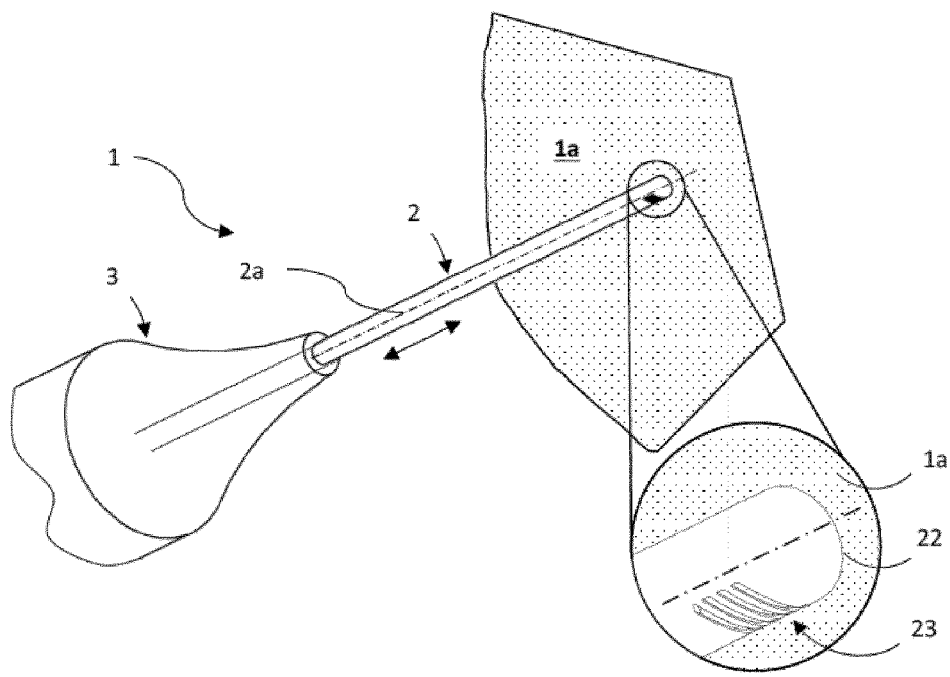
Fig. 1
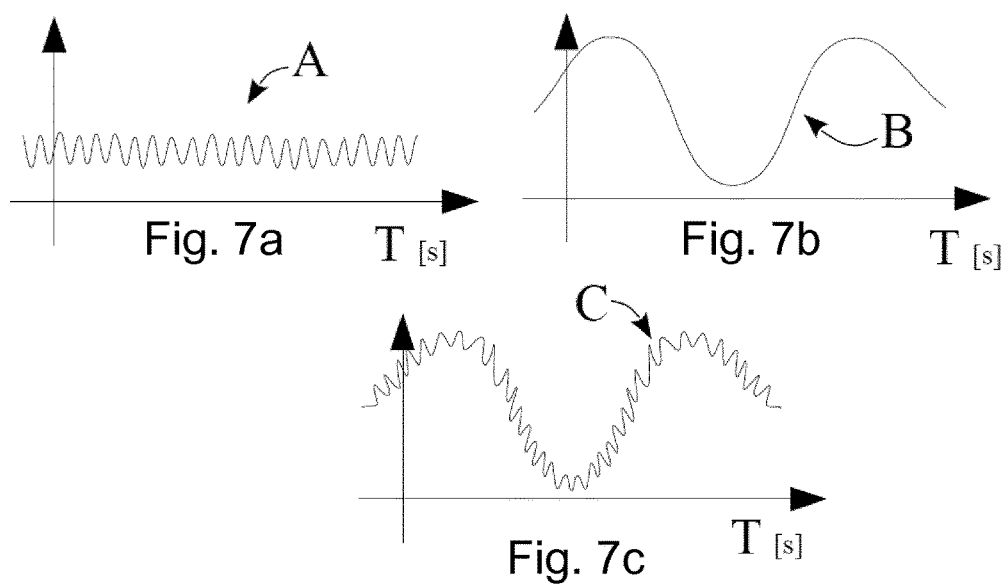
Fig. 7a  T [s]
Fig. 7b  T [s]
Fig. 7c  T [s]

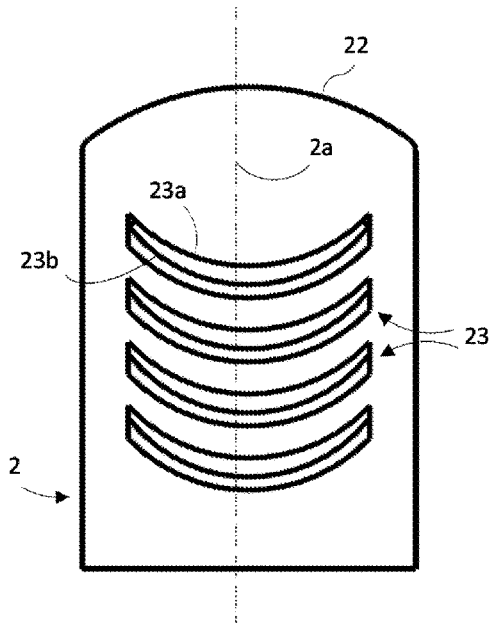
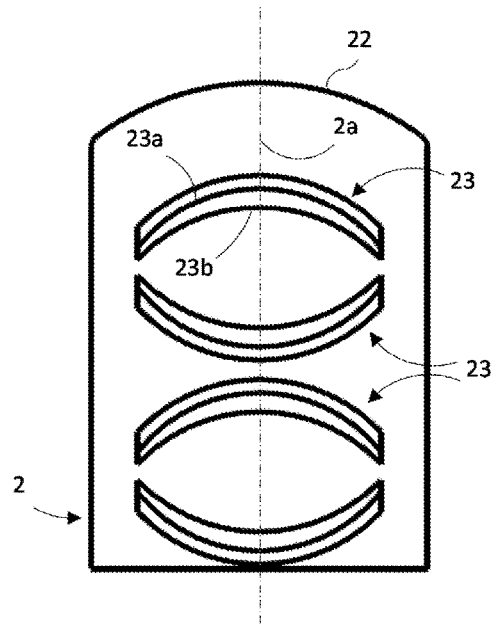
Fig. 3a
Fig. 4a
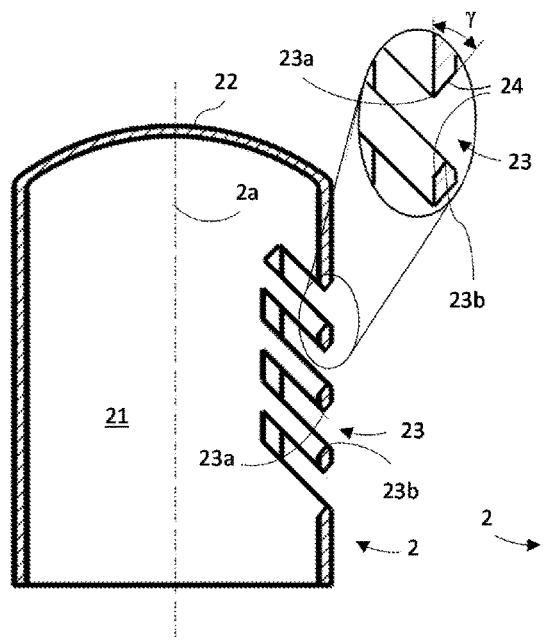
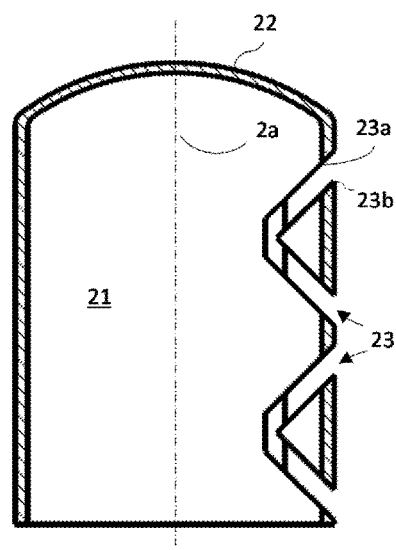
Fig. 3b
Fig. 4b

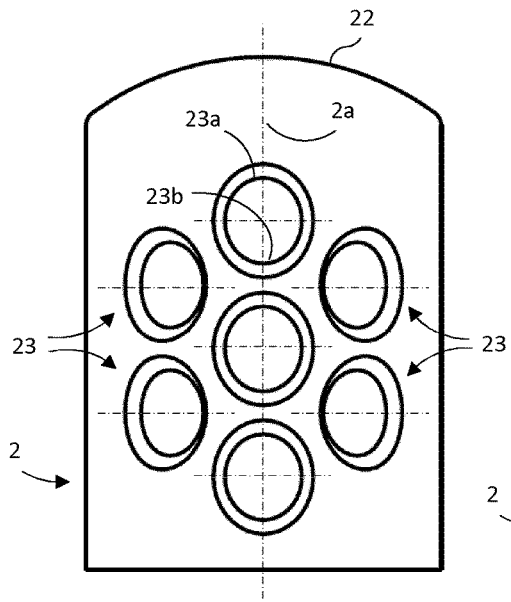
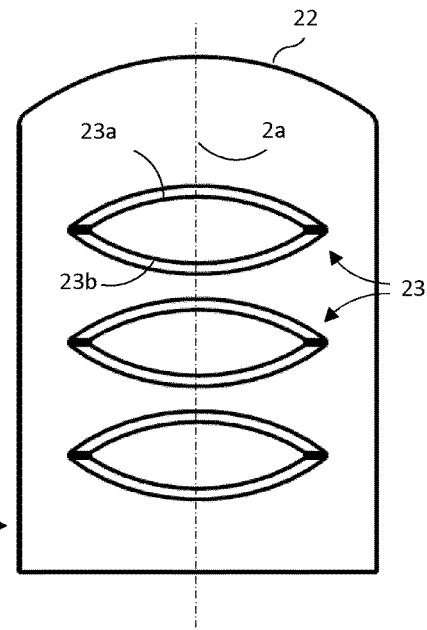
Fig. 5a  Fig. 6a
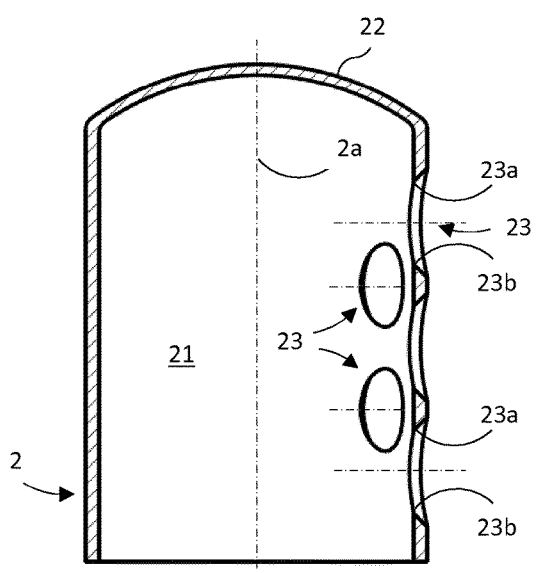
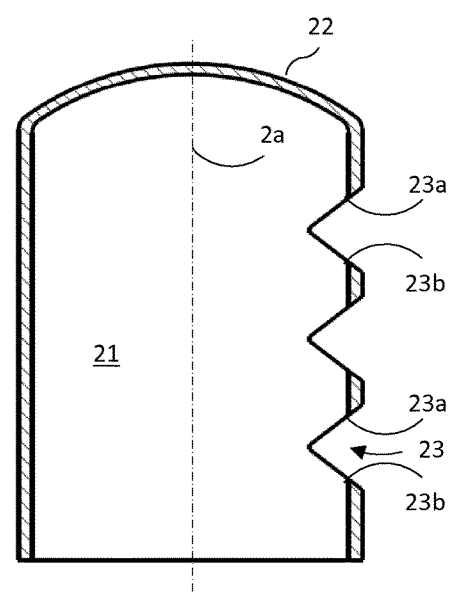
Fig. 5b  Fig. 6b

VITRECTOMY PROBE

The object of the present invention is a medical device for the excision of tissue to be mainly used in the field of Ophthalmology, i.e. Eye Surgery, and, particularly, in vitrectomy procedures. More specifically, the invention concerns a vitrectomy probe for the excision of tissues in the eye (e.g. retina and lens) and the vitreous humour (i.e. the gel filling the main cavity of the eyeball).

As it is well known, vitrectomy is a kind of eye surgery procedure required when the vitreous has become clouded following haemorrhages (e.g. as a consequence of proliferative diabetic retinopathy), inflammation or in the presence of membranes or other intraocular foreign bodies. Vitrectomy can be performed, for example, in case of conditions of the posterior chamber, such as retinal detachment with complications.

Vitrectomy involves the excision of small portions of membranes found on the retinic surface, the removal of the vitreous and its replacement with an analogous medium, called 'vitreous substitute'.

The primary tool for such surgical procedures is a vitrectomy probe, i.e. a pneumatic cutting device with a guillotine-like blade designed to perform the removal and excising operations mentioned above.

Such device includes a handle, enabling the surgeon to operate the tool; an external tube with an opening positioned on one side and close to one end of the tube; an inner tube inserted into the external one; a control system, which creates the vacuum within the two tubes and also moves the inner tube with respect to the external tube.

Specifically, through the combined effect of the two abovementioned actions, the control system enables the suction of the vitreous into the vitrectomy probe with fragments being cut by the sharp edge of the inner tube when overlapping the opening of the external tube. Such technique presents some major disadvantages.

A first drawback is due to the difficulty in changing suction speed and therefore operating with precision in the excision. Vitrectomy probes are, in fact, challenging to use and require great expertise and accuracy during the whole procedure by the surgeon. In detail, suction parameters and speed of the blade (v) determine dimensions and quantity of removed fragments. Given that the blade acts like a guillotine, the removal speed is limited (also because the flow varies sinusoidally, fluctuating between a maximum value and 0). Therefore, the vitreous, which behaves like a non-Newtonian fluid, moves and stops frequently and its viscosity varies between a maximum (when v=0) and a minimum (when v=vmax) value.

Another major drawback is related to traction forces applied to the retina, especially along its peripheral zone, where the vitreous adheres more. The removal of the vitreous in such an area puts the retina under traction forces that vary sinusoidally and can cause damage (retinal holes) or detachment.

Given the above, the purpose of the present invention is to devise a vitrectomy probe which can substantially solve the aforementioned problems. Within such purpose an important aim is to create a vitrectomy probe which is easy to use, giving surgeons great freedom of movement. Another important aim is to have a vitrectomy probe allowing fast and accurate clinical application. A further objective is to reach high flow rates. Moreover, further objective of the present invention is to have a vitrectomy probe which allows to minimize the oscillating traction forces applied to the retina.

The purpose and aims described above are achieved by a vitrectomy probe as claimed in claim 1.

Further improvements of the invention will form the subject of the dependent claims.

The characteristics of the invention and the advantages derived therefrom will be more apparent from the following description of non-limiting embodiments, illustrated in the annexed scale drawings, in which:

FIG. 1 shows a complete vitrectomy probe according to the invention;

FIGS. 2a-2d present a preferred embodiment of a vitrectomy probe according to the invention;

FIGS. 3A and 3b show a vitrectomy probe according to another embodiment of the invention;

FIGS. 4A and 4b are views of another vitrectomy probe according to the invention;

FIGS. 5A and 5b are views of a further vitrectomy probe according to the invention;

FIGS. 6A and 6b show another example of a possible implementation of a vitrectomy probe according to the invention;

Figure 2A:
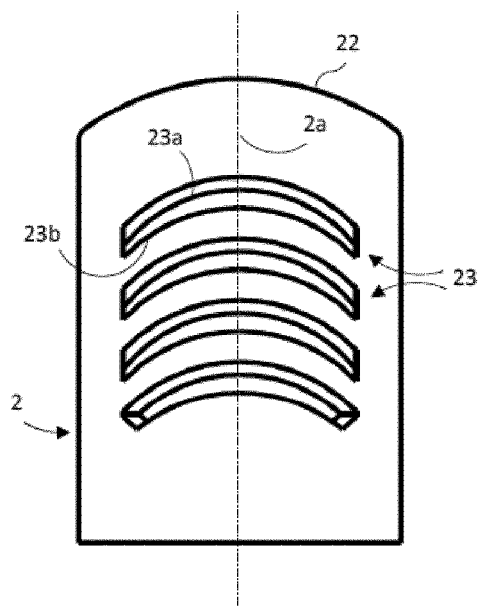

and FIGS. 7a-7c are charts describing the movement of a component of the vitrectomy probe as a function of time T [s].

The vitrectomy probe 1 as shown in FIG. 1 (from now on figures will be referred to only by their corresponding number) is adapted to be partially inserted in the eyeball so to remove the vitreous 1a, or part of it. In detail, in the present document, by "vitreous" it is meant both the clear, colourless, gelatinous mass filling ⅘ of the back of the eyeball (also called "vitreous humour" or "vitreous body") and other intraocular tissues such as the retina and the crystalline lens. Advantageously, the vitrectomy probe 1 is a single tube device. It comprises: a hollow tube 2, defining a main axis 2a, which is suitable for the excision of the said vitreous 1a; a handle 3 supporting the tube 2; a drive unit inside said handle 3 used to move tube 2 relative to the handle 3 itself; a sucking system suitable to suck the vitreous 1a in the tube 2; and a control unit conveniently connected to the drive unit and to the sucking system, the control unit operating the drive unit and the sucking system.

The free end of the tube 2 is closed and the tube 2 defines a substantially cylindrical internal passage 21 having an axis substantially parallel to the main axis 2a, and in which the removed vitreous 1a can be moved away; a closed tip 22 defining the penetrating surface of the tube 2 and, therefore, of the vitrectomy probe into the eye; one or more openings 23 enabling the vitreous to enter the internal passage 21.

It has to be emphasized that, being the vitrectomy probe 1 mono-conduit, only tube 2 is provided for being at least partially inserted into the eye, coming into direct contact with at least a part of the vitreous 1a, without other tubes interposed between the vitreous and the cutting element as in the case of the well known traditional vitrectomy probes. More precisely, the tube 2 is suitable for insertion into the eye with the closed tip 22, the openings 23 and an extended part of its external lateral surface close to the closed tip 22 coming into direct contact with the vitreous 1a, i.e. with no interposition of other tubes, such as in other known vitrectomy probes.

Each opening defines at least one cutting edge adapted to cut the vitreous 1a and, therefore, to allow it to be removed, and more precisely two cutting edges, i.e. an upper cutting edge 23a, proximal to the closed tip 22, and a lower cutting edge 23b distal from the closed tip 22 and opposite the upper cutting edge 23a so that the vitrectomy probe 1 can cut the vitreous exploiting opposite movements of the tube 2.

The openings are cut through the entire wall of the tube 2 and are placed on the lateral surface and proximal to the tip 22. Specifically, they are almost identical or, alternatively, they have different shapes and sizes. They are cut out on the same angular portion of the lateral surface with a limited extent, or, alternatively, they are on two angular portions of lateral surface that have an almost identical complementary shape.

Specifically, the said angular portion has an width substantially bigger that 120°.

The total surface of all the openings is larger than the section of the internal passage 21 and, more specifically, it ranges between 130% and 200% of the section of the internal passage 21.

The port openings 23 are transverse to the main axis 2a and, more specifically, they are inclined in respect to the main axis 2a. In detail, the openings are inclined with respect to the axis 2a by an angle α, facing the closed tip 22, substantially ranging between 5° and 175°, and more specifically, between 10° and 170°, so defining cutting edges 23a, 23b having cutting profiles inclined by an angle β smaller than 90°. Specifically, the angle of inclination α is defined by the angular portion comprised between the main axis 2a and the plane on which the cutting profiles 23a and 23b are positioned, and containing the closed tip 22.

Figure 2B:
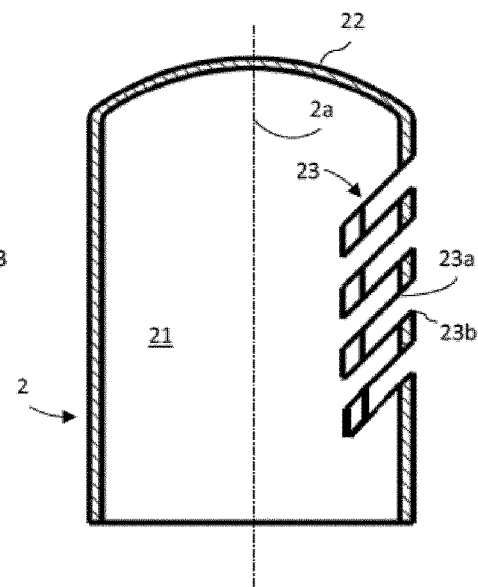
Figure 2C:
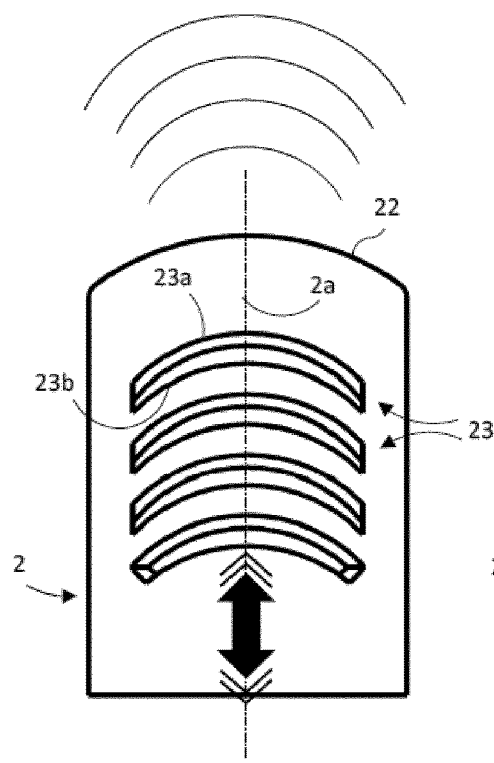
Figure 2D:
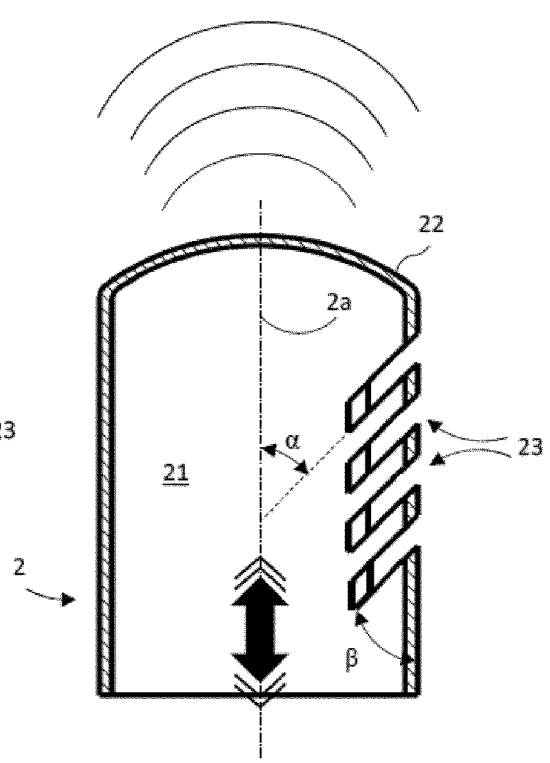

For example, (FIGS. 2a-2d, 3a and 3b) the openings 23 are parallel to each other, defining the cutting edges 23a and 23b, which are parallel to each other, reciprocally and equally spaced along the axis 2a and inclined with respect to the axis 2a by an angle of inclination α comprised between 5° and 75° or between 105° and 175°. More specifically, the angle of inclination α is almost equal to 15° or 165°. In a further embodiment, the port openings 23 define angles of inclination nearly opposite to the adjacent openings, as shown in FIGS. 4a-4b, and reciprocally spaced so as not to intersect.

Alternatively, each opening 23 has such shapes as to define cutting edges 23a and 23b substantially mirroring each other. For example (FIGS. 5A and 5b), the openings 23 can be cylindrical or, preferably, conical holes, with a radial axis (i.e. substantially perpendicular to the main axis 2a) and conveniently equidistant from one another. Alternatively, the port openings 23 present elliptical profiles equidistant from one another (FIGS. 6A and 6b).

In some cases (enlargement detail in FIG. 3b), in order to reduce the angle between the cutting profiles, the tube 2 may have a face milling 24 or another similar machining made transversally with respect to the cutting edges 23a and 23b. The face milling 24 is realized in correspondence of at least one cutting edge 23a or 23b and, preferably, in correspondence of each cutting edge 23a and 23b, in order to reduce the cutting angle β and, therefore, increase the cutting performance of the cutting edges 23a and 23b. Suitably, the face milling 24 is inclined in the opposite direction with respect to the cutting edges 23a and 23b and to the axis 2a, by an angle of levelling γ substantially comprised between 10° and 15°.

Conveniently connected to the tube 2, the vitrectomy probe 1 presents a drive unit used to move the tube 2, advantageously housed in the handle 3, and a sucking system suitable for the creation vacuum into the passage 21 so as to suck the vitreous within the tube 2. Said suction system, substantially known, includes a pump able to create said vacuum into the passage 21 and it also includes an evacuation tube connecting the pump to the internal passage 21 and allowing the evacuation of the vitreous 1a from the passage 21 and its discharge outside the vitrectomy probe 1.

The drive unit moves the tube 2 relative to the handle 3 and to the vitreous 1a defining for the tube 2 an oscillatory motion of the vibrational type A, producing pressure waves reducing the viscosity of the vitreous 1a, and a reciprocating motion B that performs a further cutting action of the vitreous 1a. Advantageously, the drive unit defines for the tube 2 a combined motion C, which is the sum of the oscillatory motion A and the reciprocating motion B which is substantially simultaneous to A and, specifically, perfectly simultaneous to A. FIGS. 7A, 7b and 7c show the movement of the tube 2 as a function of time respectively for the oscillatory motion A, the reciprocating motion B and the combined motion C. Preferably, A and B are both translational motions and, particularly, both define an axis of movement, which is parallel to the main axis 2a. Alternatively, motion A is translational along said axis of movement while B is a type of rotational motion around the said axis of movement. The oscillatory motion A and the reciprocating motion B are characterized by sonic frequencies (substantially comprised between 20 Hz and 20 kHz) and/or ultrasonic (substantially comprised between 20 kHz and 2 MHz) frequencies. In detail, the oscillatory motion A has a higher frequency than the reciprocating motion B. More specifically, motion A has a frequency which is substantially at least three times higher and, more precisely, substantially at least ten times higher than the frequency of the reciprocating motion B.

More in detail, the oscillatory motion A has a frequency of at least 1 kHz, preferably substantially at least equal to 3 kHz, more preferably substantially at least equal to 5 kHz and, more preferably still, at least equal to 10 kHz. The reciprocating motion B has a frequency substantially lower that 3 kHz, preferably substantially lower that 1.5 kHz, more preferably substantially not higher than 0.9 kHz.

The amplitude of the oscillatory motion A is small and moreover the oscillatory motion A presents an amplitude which is smaller that the amplitude of the reciprocating motion B. More precisely, the amplitude of the reciprocating motion B is substantially at least double the amplitude of the oscillatory motion A and, specifically, it is five times bigger.

Still more precisely, the amplitude of the reciprocating motion B is substantially at least equal to the maximum distance, measured along the axis 2a, between the upper cutting edge 23a and the lower cutting edge 23b belonging to the same port opening 23.

In detail, the amplitude of the oscillatory motion A is substantially not higher than 0.5 mm, particularly substantially lower than 0.1 mm and more particularly 0.05 mm; while the amplitude of the reciprocating motion B is substantially comprised between 0.05 mm and 2.5 mm and, particularly between 0.1 mm and 0.3 mm. Alternatively, the amplitude of the reciprocating motion B is substantially comprised between 0.01 and 0.5 mm and, in detail, between 0.1 and 0.1 mm.

The drive unit includes at least one actuator suitable to selectively perform one of the motions A, B and C and at least one guideway, preferably only one, defining said axis of movement for the tube 2.

The drive unit can include two actuators, one for motion A and one for motion B, working separately or jointly to define the combined motion C. Alternatively, the drive unit can have a single actuator fit for one of the motions A, B and C selectively. Said guide is formed inside the handle 3; it is preferably prismatic and defines a cavity in which the tube 2 can only run along the axis of movement. In a non limiting example, this is done through the use of grooved splines, protrusions, angular stop elements, bonded joints.

It has to be underlined that, if two actuators are used, the first actuator implementing the oscillating motion A is integral to the tube 2, while the second actuator defining the reciprocating motion B is integral to the first actuator and thus to the tube 2.

With both one and two actuators, these include electrical, pneumatic, magnetostrictive and/or piezoelectric drive systems conveniently operated through periodical input wave signals with various profiles. Non limiting examples include sinusoidal, saw-toothed, trapezoidal, triangular, square and step profiles. Preferably, in the instance of a single actuator, this is piezoelectric.

The control unit is suitably connected to the drive system to operate it. Particularly, the control unit allows to regulate at least one between the frequency and the amplitude of at least one of the motions A, B and C and, preferably it allows to vary the frequency and the amplitude of the oscillatory motion A, of the reciprocating motion B and, therefore, also of the combined motion C.

The control unit includes an electronic board adapted to control said drive unit and control means enabling a surgeon to select one of the motions A, B or C, during a surgical procedure as well, and, preferably, to vary their frequency and amplitude.

Such control means can be knobs, switchboards, pedals and other similar elements allowing said regulation and suitably connected with the handle 3.

Additionally, the control means and, therefore, the control unit are connected to the suction system so to operate and regulate the vacuum level into the internal passage 21.

According to an embodiment, the control unit may be interfaced with an echo unit able to emit and receive ultrasound (ultrasonic waves) in order to determine the distance between the probe and the retina according to known ultrasound techniques. The echo unit advantageously comprises one or more ultrasound transducers that may also partly coincide with the actuators that generate the vibrational motion, for example on the tip. Thanks to what described above, it is possible to provide a feedback control of the action of the vitrectomy probe 1, that is, it is possible to provide a warning signal, or directly stop a single motion among A, B and C or all the motions A, B and C of the tube 2, if the end of the vitrectomy probe and, more particularly, the free end of the tube 2, is too close to the retina or to other critical parts of the eye in order to prevent their damage.

The vitrectomy probe, whose structure has been described above, works in the following way.

First of all, the surgeon grasps the handle 3 and inserts the tube 2 into the eye putting the vitreous into direct contact with at least a part of the external lateral surface of the tube 2 and, therefore, with the closed tip 22 and with the openings 23. Then, through the control unit, the surgeon control the activation of the suction system, which creates the vacuum within the internal passage 21 and begins to suck the vitreous 1*a* into the tube 2 through the openings 23. At the same time, again through the control unit, the surgeon sets the vibrational motion A of the tube 2, which moves according to the pattern shown in FIG. 7*a*. Due to its said frequency, such motion of the tube 2 creates pressure waves that reduce the viscosity of the vitreous 1*a* and, in detail, they colliquate the vitreous 1*a*, whose viscosity, in turn, significantly diminishes, possibly resembling the viscosity of water. Due to its condition described above, the vitreous 1*a* can be drawn into the internal passage 21 by the vacuum generated therein and, therefore, a convenient and safe removal can be carried out. Additionally, to increase suction flow rate and/or to remove solid or particularly viscous fragments that can not be aspirated by said vacuum, the surgeon can activate the combined motion C, i.e. the substantially simultaneous implementation of vibrational motion A and reciprocating motion B (as shown in FIG. 7*c*). The reciprocating motion B enables at least one of the cutting edges 23*a* and 23*b*, and specifically, the cutting edges 23*a* and 23*b* to cut in turns the vitreous 1*a* while this enters the internal passage 21 through the openings 23.

Specifically, the parts of vitreous 1*a* that are solid or particularly viscous enter the internal passage 21 through the openings 23 and, being stretched by the pulling action of the vacuum inside the passage 21, they undergo a cutting action by the cutting edges 23*a* and 23*b* that behave like a sliding blade, such as when a shaving knife draws across the skin to cut facial hair (without using electric shaver).

Once such solid or high density fragments have been removed, the surgeon stops the reciprocating motion B and, therefore, continues the procedure with the help of the single vibrational motion A of the tube 2.

It has to be underlined that the surgeon can carry out the whole surgical procedure with the exclusive use of the combined motion C (FIG. 7*c*) on the tube 2 or, alternatively, he/she can use the single reciprocating motion B either at certain stages or throughout the procedure (FIG. 7*b*).

The vitrectomy probe 1 offers some major advantages. First of all, the vitrectomy probe 1 allows the excision of the vitreous with minimal traction forces on the retina, therefore reducing stress and strain on the eye.

The above advantage is achieved with the creation of a single-tube vitrectomy probe, characterized in that it is possible to switch motions A and B and featuring the innovative combined motion C. In fact, the oscillatory motion A enables the tube 2 to behave as a generator of waves propagating in the vitreous and making it vibrate. Said vibration determines a change in the characteristics of the vitreous 1*a* partly breaking the bonds and decreasing its viscosity. As a consequence, the vitreous 1*a* behaves like a thixotropic fluid in which the waves—sonic or ultrasonic—cause the collagen fibers and the filaments of hyaluronic acid to slide, inducing an interruption in the existing bonds and triggering the decrease of the viscosity and an increase in the sliding. Such altered vitreous can be most easily removed placing the vitrectomy probe 1 in the eyeball in any way, keeping the aspiration flow at very high rate. The reciprocating motion B significantly contributes to the removal of the vitreous in general and, more in detail, of solid and semi-solid residues that the pressure waves generated by the vibrational motion A have not dissolved.

The efficiency of the behaviour described above is increased further by operating the single actuator or the actuators according to periodical input wave signals with various profiles, for example, but not limiting to, sinusoidal, saw-toothed, trapezoidal, triangular, square and step profiles. Another advantage is therefore that all the motions (vibrational A, reciprocating B and combined C) define a seamless cutting action, and in detail, a perfectly continuous cutting action of the filaments of the vitreous 1*a*.

Furthermore, because it has only one tube 2, the vitrectomy probe 1 does not perform a guillotine-like cutting action, and this leads to a reduction of the stress to the eye.

As a matter of fact, the reciprocating motion B enables the cutting edges 23*a* and 23*b* to perform a vibrating-blade cutting action, therefore with a reduced negative impact.

Moreover, the achieved high flow rate values allow to contain the overall dimensions of the vitrectomy probe and specifically the external diameter of the tube 2; such reduction in size enables to make smaller surgical incisions on the external surface of the eye so that these can be sutureless, generally entailing smaller injuries for the eye.

Then an important advantage is constituted by the ability of the vitrectomy probe 1 to perform fast, accurate and very safe vitrectomy procedures with a strong reduction in the intra- and post-operative complications for the patient.

A not secondary advantage is given by the control unit and, specifically, by the control means that allow to vary amplitude and frequency of the said motions A, B and C, also during a procedure, enabling to adjust suction speed depending on specific needs.

The invention claimed is:

1. Vitrectomy probe for removing the vitreous humour comprising a single closed-tip tube adapted to be put into direct contact, at least partially, with said vitreous, defining a main axis and including an internal passage and at least one lateral opening to enable said vitreous to enter the internal passage; a suction system for the creation of vacuum within said internal passage sucking said vitreous into said opening; wherein said at least one opening comprises at least one cutting edge; and wherein the probe comprises a drive unit adapted to move said tube with a vibrational motion (A), which vibration motion generates pressure waves reducing the viscosity of said vitreous, and a reciprocating motion (B), which reciprocating motion allows at least one cutting edge to cut said vitreous; and wherein said vibrational motion (A) has a frequency which is higher than the frequency of said reciprocating motion (B).

2. Vitrectomy probe according to claim 1, wherein said drive system is configured to move said tube with a combined motion (C), which is the sum of said vibrational motion (A) and said reciprocating motion (B).

3. Vitrectomy probe according to claim 1, wherein said vibrational motion (A) has a frequency which is substantially three times higher than the frequency of said reciprocating motion (B).

4. Vitrectomy probe according to claim 1, wherein said vibrational motion (A) has a frequency at least equal to 3 kHz and said reciprocating motion (B) has a frequency lower than 1.5 kHz.

5. Vitrectomy probe according to claim 4, wherein said frequency of said vibrational motion (A) is at least equal to 10 kHz and said reciprocating motion (B) has a frequency not higher than 0.9 kHz.

6. Vitrectomy probe according to claim 1, wherein the amplitude of said reciprocating motion (B) is at least five times the amplitude of said vibrational motion (A).

7. Vitrectomy probe according to claim 1, wherein the amplitude of said vibrational motion (A) is lower than 0.1 mm and the amplitude of said reciprocating motion (B) is between 0.05 mm and 2.5 mm.

8. Vitrectomy probe according to claim 1, wherein the vibrational motion (A) and the reciprocating motion (B) are translational.

9. Vitrectomy probe according to claim 1, further comprising a face, which is transverse to at least one of said cutting edges.

10. Vitrectomy probe according to claim 1, wherein the opening or the openings are inclined, with respect to the main axis, by an angle a ranging between 5° and 175°.

11. Vitrectomy probe according to claim 1, further comprising a control unit adapted to regulate at least one between said frequency and said amplitude of at least one of said motions (A, B).

12. Vitrectomy probe according to claim 11, wherein said control unit includes control means for said regulation, such as knobs, switches, or pedals.

13. Vitrectomy probe according to claim 1, wherein the opening or the openings are inclined, with respect to the main axis, by an angle a ranging between 10° and 170°, so as to define cutting edges having cutting profiles inclined by an angle β smaller than 90°.

14. Vitrectomy probe according to claim 1, comprising a handle supporting the single closed-tip tube and wherein the drive unit moves the single closed-tip tube relative to the handle.

15. Vitrectomy probe for removing the vitreous humour comprising:
   a tube adapted to be put into direct contact, at least partially, with said vitreous, defining a main axis and including an internal passage and at least one opening to enable said vitreous to enter the internal passage, wherein said at least one opening is shaped in such a way as to perform a cutting action through at least one cutting edge;
   a suction system for the creation of vacuum within said internal passage sucking said vitreous into said opening;
   a drive unit adapted to move said tube with a vibrational motion (A), which vibration motion generates pressure waves reducing the viscosity of said vitreous, and a reciprocating motion (B), which reciprocating motion allows at least one cutting edge to cut said vitreous, wherein said vibrational motion (A) has a frequency which is higher than the frequency of said reciprocating motion (B);
   a control unit adapted to regulate at least one between the frequency and the amplitude of at least one of said motions (A, B);
   an echo unit able to transmit ultrasounds toward a target of a patient's body and to receive echo signals from the target itself through one or more piezoelectric transducers;
   wherein the control unit is interfaced with the echo unit and arranged to process the received echo signals to determine the distance of the target, the control unit being interfaced to said echo unit to provide a warning signal or cause blocking of one among the motions A, B and/or C or of all the motions (A, B, C) if the target is too close, and wherein motion (C) is a combined motion which is the combination of said vibrational motion (A) and said reciprocating motion (B).

16. Vitrectomy probe according to claim 15, wherein the target is the retina, the warning signal or the block signal being generated by the control unit when the tube is located within the eye cavity at a distance from the retina that is less than a predefined amount.

17. Vitrectomy probe according to claim 15, wherein one or more transducers of the echo unit are responsible of the vibrational motion (A).

18. Vitrectomy probe according to claim 15, wherein the target is a retina of the patient.

* * * * *